United States Patent
Xu et al.

(10) Patent No.: US 10,191,026 B2
(45) Date of Patent: Jan. 29, 2019

(54) FRUIT AND VEGETABLE SUGAR CONTENT DETECTOR

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Rui Xu, Beijing (CN); Shijun Wang, Beijing (CN); Xuewen Lv, Beijing (CN); Xuerong Wang, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 145 days.

(21) Appl. No.: 15/301,422

(22) PCT Filed: Nov. 6, 2015

(86) PCT No.: PCT/CN2015/093939
§ 371 (c)(1),
(2) Date: Oct. 3, 2016

(87) PCT Pub. No.: WO2016/206276
PCT Pub. Date: Dec. 29, 2016

(65) Prior Publication Data
US 2017/0131255 A1    May 11, 2017

(30) Foreign Application Priority Data
Jun. 24, 2015 (CN) .......................... 2015 1 0354495

(51) Int. Cl.
*G01N 33/02* (2006.01)
*G01N 27/04* (2006.01)
*G01N 27/06* (2006.01)

(52) U.S. Cl.
CPC ............ *G01N 33/025* (2013.01); *G01N 27/04* (2013.01); *G01N 27/041* (2013.01); *G01N 27/045* (2013.01); *G01N 27/06* (2013.01)

(58) Field of Classification Search
CPC ..... G01N 27/041; G01N 27/045; G01N 27/06
See application file for complete search history.

(56) References Cited

U.S. PATENT DOCUMENTS

| 4,047,100 A | 9/1977 | Robinson |
| 5,189,366 A * | 2/1993 | Mayo ................... G01N 27/023 324/225 |

(Continued)

FOREIGN PATENT DOCUMENTS

| CN | 1937956 A | 3/2007 |
| CN | 101393154 | 3/2009 |

(Continued)

OTHER PUBLICATIONS

First Office Action for Chinese Application No. 201510354495.2, dated Apr. 6, 2017, 8 Pages.

(Continued)

*Primary Examiner* — Giovanni Astacio-Oquendo
*Assistant Examiner* — Alvaro Fortich
(74) *Attorney, Agent, or Firm* — Brooks Kushman P.C.

(57) ABSTRACT

A fruit and vegetable sugar content detector is provided, which includes a measurement electrode unit including two measurement electrodes capable of being inserted into a to-be-detected fruit or vegetable, one end of one of the two measurement electrodes being connected to one end of the other one of the two measurement electrodes, a resistance (Continued)

detection circuit connected to the measurement electrode unit and configured to detect a resistance between the two measurement electrodes, and a processor connected to the resistance detection circuit and configured to determine, in accordance with the detected resistance between the two measurement electrodes, a sugar content of the to-be-detected fruit or vegetable, and generate sugar content indication information.

12 Claims, 5 Drawing Sheets

(56) References Cited

U.S. PATENT DOCUMENTS

2013/0225957 A1* 8/2013 Kawamoto .......... A61B 5/1411
                                                              600/347
2017/0010296 A1* 1/2017 Shimokawa .......... A01G 22/00
2017/0131255 A1    5/2017 Xu et al.

FOREIGN PATENT DOCUMENTS

| CN | 104880491 A  | 9/2015 |
| CN | 204789444 U  | 11/2015 |
| JP | S6385342 A   | 4/1988 |
| KR | 20140036470 A | 3/2014 |

OTHER PUBLICATIONS

International Search Report and Written Opinion for Application No. PCT/CN2015/093939, dated Mar. 22, 2016, 14 Pages.

The Design and Research in the Electrical Conductivity INstrument based on Embedded System, Zeng Mingmin, China Academic Journal Electronic Publishing House, dated Jan. 15, 2013, Guangzhou, China, 26 pages.

* cited by examiner

FRUIT AND VEGETABLE SUGAR CONTENT DETECTOR

CROSS-REFERENCE TO RELATED APPLICATION

This application is the U.S. national phase of PCT Application No. PCT/CN2015/093939 filed on Nov. 6, 2016, which claims priority to Chinese Patent Application No. 201510354495.2 filed on Jun. 24, 2015, the disclosures of which are incorporated in their entirety by reference herein.

TECHNICAL FIELD

The present disclosure relates to the field of health care technology, in particular to a fruit and vegetable sugar content detector.

BACKGROUND

Along with the improvements of people's living standard, rates of diseases caused by unreasonable dietary structure are increasing too. Diabetes currently becomes a common disease to middle aged and elderly people, and even to young people. For the prevention of diabetes, it is necessary to control a daily intake of sugar within a reasonable range. Fruits and vegetables, especially the fruits, are foods having a relatively large sugar content, so people is required to pay attention to these foods. However, it is currently impossible to acquire the sugar content of the fruits and vegetables conveniently and accurately.

SUMMARY

In view of the above, a fruit and vegetable sugar content detector is provided in the present disclosure, so as to detect sugar contents of fruits and vegetables conveniently and accurately.

In one aspect, the present disclosure provides in some embodiments a fruit and vegetable sugar content detector, including: a measurement electrode unit including two measurement electrodes capable of being inserted into a to-be-detected fruit or vegetable, one end of one of the two measurement electrodes being connected to one end of the other one of the two measurement electrodes; a resistance detection circuit connected to the measurement electrode unit and configured to detect a resistance between the two measurement electrodes; and a processor connected to the resistance detection circuit and configured to determine, in accordance with the detected resistance between the two measurement electrodes, a sugar content of the to-be-detected fruit or vegetable, and generate sugar content indication information.

Optionally, the fruit and vegetable sugar content detector further includes a storage connected to the processor and configured to store therein a correspondence between the resistance and the sugar content. The processor is configured to inquire the correspondence stored in the storage in accordance with the detected resistance between the measurement electrodes, and determine the sugar content of the to-be-detected fruit or vegetable.

Optionally, the measurement electrodes are each of a cylindrical shape, and a cross section of each measurement electrode has a diameter within a range from 5 μm to 15 μm.

Optionally, the measurement electrodes are each made of a metal.

Optionally, the fruit and vegetable sugar content detector further includes an indicator connected to the processor and configured to indicate the sugar content indication information.

Optionally, the indicator is a display, a sound player, or a combination thereof.

Optionally, the fruit and vegetable sugar content detector further includes a communicator connected to the processor and configured to transmit the sugar content indication information to an electronic terminal, so as to enable the electronic terminal to perform indication in response toe the sugar content indication information.

Optionally, the resistance detection circuit includes: an oscillator configured to generate a voltage signal; a fixed resistor, one end of which is connected to the oscillator and the other end of which is connected to the measurement electrode unit; a phase sensitive detector connected to the measurement electrode unit and configured to filter a voltage signal from the measurement electrode unit, so as to remove a first voltage signal related to a capacitance between the two measurement electrodes, and reserve a second voltage signal related to the resistance between the two measurement electrodes; and an analog-to-digital converter connected to the phase sensitive detector and configured to convert the second voltage signal into a digital voltage value. The processor is connected to the analog-to-digital converter and configured to determine, based on the digital voltage value, the resistance between the two measurement electrodes using an equation $$R_x = \frac{R_f * V_o}{V_I},$$

where $R_x$ represents the resistance between the two measurement electrodes, $V_I$ represents a voltage value of the voltage signal generated by the oscillator, $V_o$ represents the digital voltage value, and $R_f$ represents a resistance of the fixed resistor.

Optionally, the resistance detection circuit further includes an operational amplifier arranged between the measurement electrode unit and the phase sensitive detector and configured to amplify the voltage signal from the measurement electrode unit and output the amplified voltage signal to the phase sensitive detector.

Optionally, the measurement electrode unit further includes a measurement column arranged between and connected to the two measurement electrodes. The processor is further configured to determine, based on the resistance between the two measurement electrodes, a resistivity of the to-be-detected fruit or vegetable using an equation $$\rho = \frac{V_o * R_f * S}{V_I * L}$$

and determine the sugar content of the to-be-detected fruit or vegetable in accordance with the resistivity, where ρ represents the resistivity of the to-be-detected fruit or vegetable, $R_f$ is of a value within the range from 10Ω to 100Ω, S represents a sectional area of the measurement column, and L represents a length of the measurement column.

Optionally, the fruit and vegetable sugar content detector further includes a storage connected to the processor and configured to store therein a correspondence between the resistivity and the sugar content, and the processor is further configured to inquire the correspondence stored in the storage in accordance with the resistivity of the to-be-detected fruit or vegetable, and determine the sugar content of the to-be-detected fruit or vegetable.

Optionally, the fruit and vegetable sugar content detector further includes: an accumulator connected to the processor and configured to accumulate sugar contents of the fruit or vegetable detected within a predetermined time period to acquire an accumulated value; a comparator connected to the accumulator and configured to compare the accumulated value with a sugar content threshold, and generate alarm information in the case that the accumulated value exceeds the sugar content threshold; and an alarm connected to the comparator and configured to send an alarm in accordance with the alarm information.

In another aspect, the present disclosure provides in some embodiments a wearable electronic device, including: the above-mentioned fruit and vegetable sugar content detector; a housing; a groove arranged on the housing and configured to receive the two measurement electrodes of the measurement electrode unit of the fruit and vegetable sugar content detector, the two measurement electrodes having a first state where the two measurement electrodes are received in the groove and a second state where the two measurement electrodes extend out of the groove; and a control member arranged on the housing, connected to the measurement electrode unit, and configured to switch the two measurement electrodes between the first state and the second state.

Optionally, the control member is an elastic button.

According to the technical solutions of the present disclosure, the sugar content of the to-be-detected fruit or vegetable may be detected conveniently and accurately, and the sugar content indication information may be generated and shown to a user. As a result, it is able to help the user to control sugar intake.

DETAILED DESCRIPTION OF THE EMBODIMENTS

A fruit or vegetable may contain juice more or less, and the juice is electrically conductive to some extent. In addition, a sugar component contained in the juice is not electrically conductive, and the more the sugar content, the larger the resistance. Based on this, in embodiments of the present disclosure, the sugar content of the fruit or vegetable may be determined by detecting a resistance of the fruit or vegetable, and a sugar content indication information may be generated and shown to a user.

The present disclosure will be described hereinafter in conjunction with the drawings and embodiments. The following embodiments are for illustrative purposes only, but shall not be used to limit the scope of the present disclosure.

Figure 1:
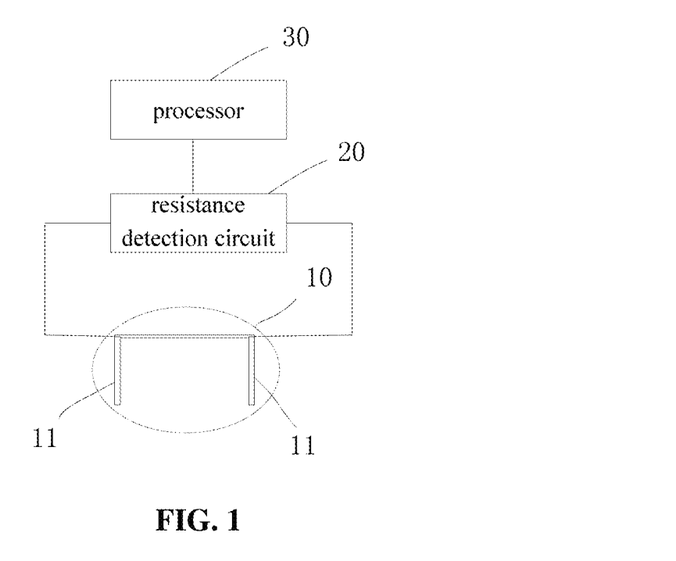
FIG. 1 is a schematic view showing a fruit and vegetable sugar content detector according to an embodiment of the present disclosure.

The present disclosure provides in some embodiments a fruit and vegetable sugar content detector which, as shown in FIG. 1, includes: a measurement electrode unit 10 including two measurement electrodes 11 capable of being inserted into a to-be-detected fruit or vegetable, one end of one of the two measurement electrodes 11 being connected to one end of the other one of the two measurement electrodes 11; a resistance detection circuit 20 connected to the measurement electrode unit 10 and configured to detect a resistance between the two measurement electrodes 11; and a processor 30 connected to the resistance detection circuit 20 and configured to determine, in accordance with the detected resistance between the two measurement electrodes 11, a sugar content of the to-be-detected fruit or vegetable, and generate sugar content indication information.

The measurement electrodes 11 may be each made of a metal material with excellent electrical conductivity, e.g., copper or silver. Each measurement electrode may be of a cylindrical shape, and a cross section of each measurement electrode may be of a diameter within a range from 5 to 15 μm, and optionally 10 μm. Because the diameter of the cross section of the measurement electrode is relatively small, it is able to prevent the fruit or vegetable from being damaged seriously after inserting the measurement electrodes inside the fruit or vegetable. The ends of the measurement electrodes may be connected to each other via a wire or any other conductor.

The sugar content indication information generated by the processor 30 may be information about the resistance detected by the resistance detection circuit 20. Optionally, the processor 30 may convert the information about the resistance detected by the resistance detection circuit 20 into comprehensible sugar content information, e.g., 4% or 7%, or level one or level two (the higher the level, the larger the sugar content).

Figure 12:
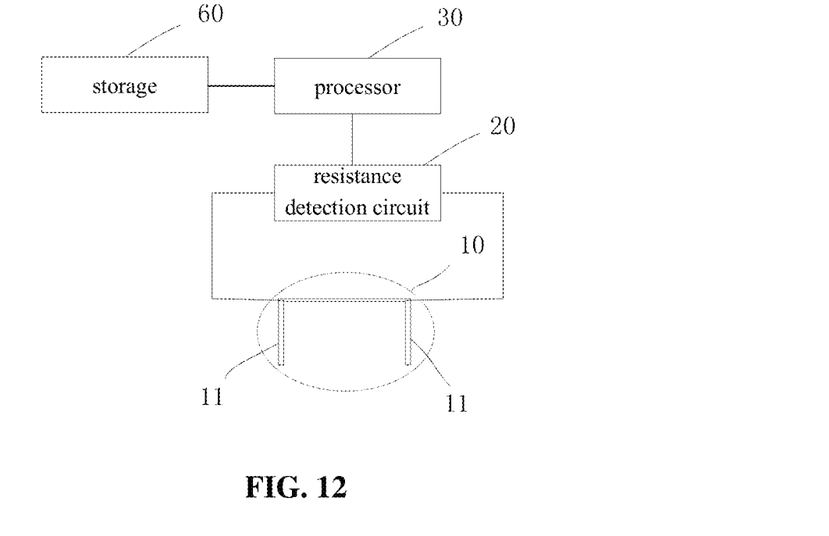
FIG. 12 is still yet another schematic view showing a fruit and vegetable sugar content detector according to an embodiment of the present disclosure.

To be specific, referring to FIG. 12, the fruit and vegetable sugar content detector may include a storage 60 connected to the processor 30 and configured to store therein a correspondence between the resistance and the sugar content. The processor 30 may inquire the correspondence stored in the storage 60, and determine the sugar content of the to-bedetected fruit or vegetable corresponding to the resistance detected by the resistance detection circuit 20. Of course, in some other embodiments of the present disclosure, the storage 60 may also be built in the processor 30.

Of course, the processor 30 may convert the information about the resistance detected by the resistance detection circuit 20 into the sugar content information with any other approaches, e.g., through a predetermined conversion equation.

According to the fruit and vegetable sugar content detector in the embodiments of the present disclosure, it is able to detect the sugar content of the fruit or vegetable conveniently and accurately, and generate the sugar content indication information for the user, thereby helping the user to control the sugar intake.

Figure 2:
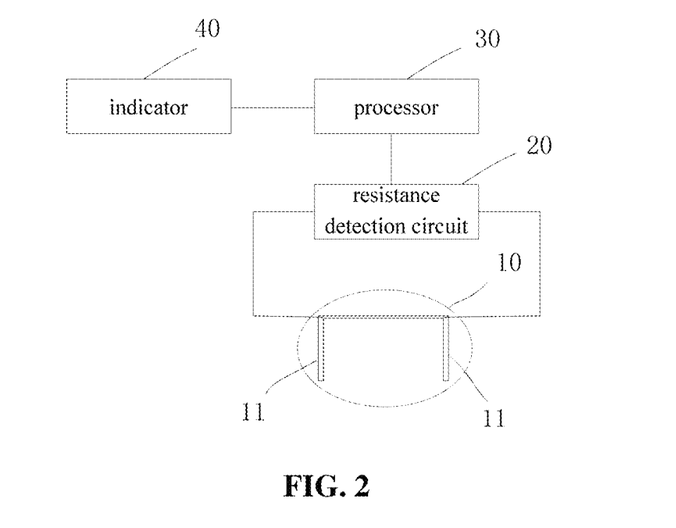
FIG. 2 is another schematic view showing a fruit and vegetable sugar content detector according to an embodiment of the present disclosure.

Referring to FIG. 2, in an embodiment of the present disclosure, the fruit and vegetable sugar content detector may include an indicator 40 connected to the processor 30 and configured to perform indication according to the sugar content indication information. Optionally, the indicator 40 is a display, a sound player or a combination thereof.

In the embodiment of the present disclosure, it is able for the fruit and vegetable sugar content detector to indicate the sugar content indication information through the indicator thereof, without help from any other devices, so the implementation is simple.

Figure 3:
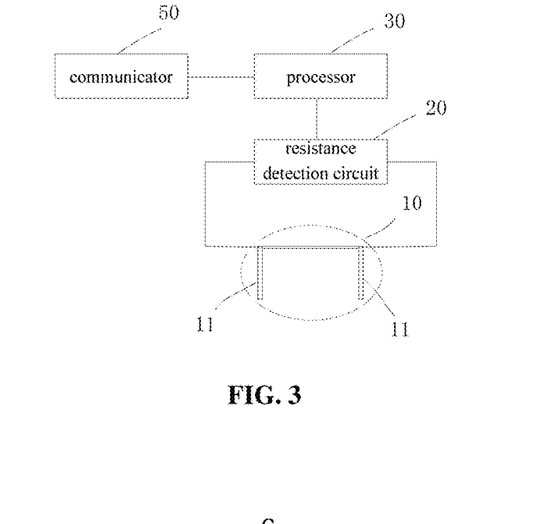
FIG. 3 is yet another schematic view showing a fruit and vegetable sugar content detector according to an embodiment of the present disclosure.

Referring to FIG. 3, in an embodiment of the present disclosure, the fruit and vegetable sugar content detector may include a communicator 50 connected to the processor 30 and configured to transmit the sugar content indication information to an electronic terminal, so as to enable the electronic terminal to perform indication according to the sugar content indication information. Optionally, the communicator 50 is a wireless communicator that is connected to the electronic terminal in a wireless manner. Optionally, the electronic terminal is a mobile phone.

In the embodiment of the present disclosure, the fruit and vegetable sugar content detector cooperates with the electronic terminal, so as to indicate the sugar content indication information. Through the electronic terminal, it is able to indicate the sugar content indication information in various ways. In addition, usually the electronic terminal has relatively strong processing capacity, so it may be used to analyze and process, e.g., summarize, the sugar contents detected by the fruit and vegetable sugar content detector.

The structure of the resistance detection circuit 20 in the embodiments of the present disclosure will be described hereinafter.

Figure 4:
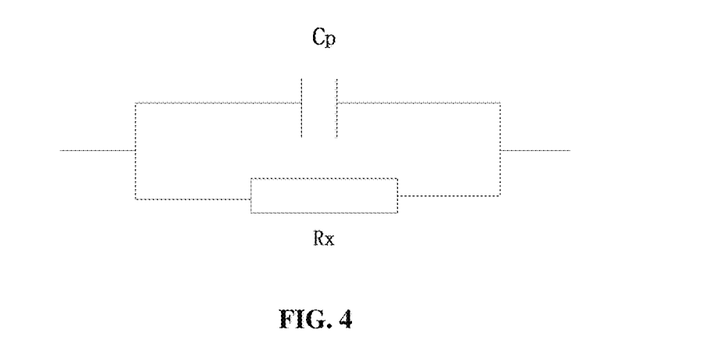
FIG. 4 is an equivalent circuit diagram of a resistance of a measurement electrode unit according to an embodiment of the present disclosure.

A detection result of the resistance detection circuit 20 may be affected by a capacitance between the two measurement electrodes, so the resistance between the two measurement electrodes may not be equivalent to the resistance of the to-be-detected fruit or vegetable. Referring to FIG. 4, which is an equivalent circuit diagram of the resistance of the measurement electrode unit 10, $R_x$ represents the resistance between the two measurement electrodes, and $C_p$ represents the capacitance between the two measurement electrodes. In the case that the resistance $R_x$ between the two measurement electrodes is of a relatively small value, the capacitance $C_p$ therebetween can be neglected. In the case that the resistance $R_x$ between the two measurement electrodes is of a relatively large value, the capacitance $C_p$ therebetween cannot be neglected.

In an embodiment of the present disclosure, a voltage signal, e.g., a sine pulse signal or a cosine pulse signal may be inputted into the measurement electrode unit 10. In the case that the voltage signal is transmitted through a capacitor, a phase of the voltage signal may be shifted by 90 degrees, and in the case that the voltage signal is transmitted through a resistor, its phase may not be shifted. Based on this principle, a phase sensitive detector may be provided, so as to remove a voltage signal component related to the capacitance between the two measurement electrodes and merely reserve a voltage signal component related to the resistance between the two measurement electrodes, thereby calculating the resistance between the two measurement electrodes accurately.

Figure 5:
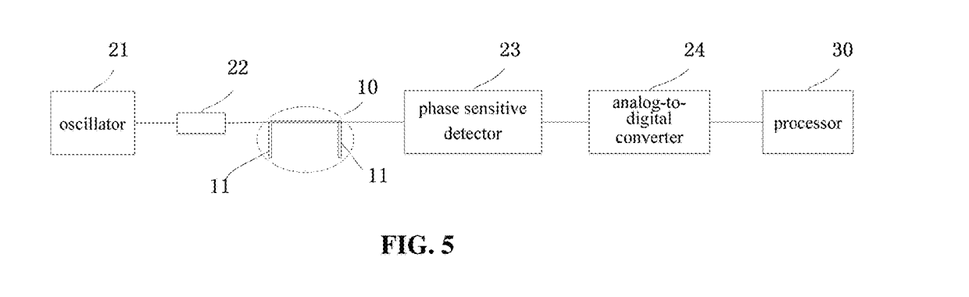
FIG. 5 is a schematic view showing a resistance detection circuit according to an embodiment of the present disclosure.
Figure 6:
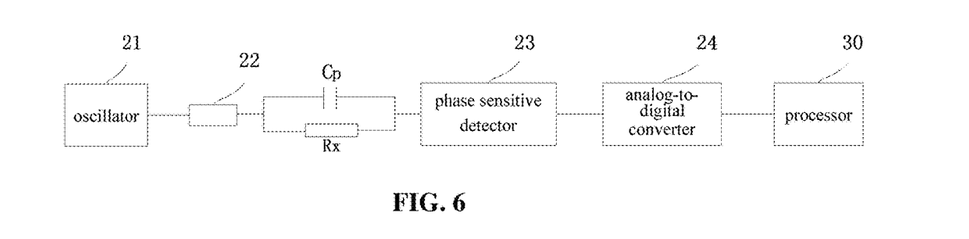
FIG. 6 is an equivalent circuit diagram of the resistance detection circuit in FIG. 5.

Referring to FIG. 5 which is a schematic view showing the resistance detection circuit and FIG. 6 which is an equivalent circuit diagram of the resistance detection circuit in FIG. 5 according to an embodiment of the present disclosure, the resistance detection circuit includes an oscillator 21 configured to generate a voltage signal; a fixed resistor 22, one end of which is connected to the oscillator 21 and the other end of which is connected to the measurement electrode unit 10; a phase sensitive detector 23 connected to the measurement electrode unit 10 and configured to filter the voltage signal from the measurement electrode unit 10, so as to remove a first voltage signal related to the capacitance between the two measurement electrodes 11, and reserve a second voltage signal related to the resistance between the two measurement electrodes 11; and an analog-to-digital converter 24 connected to the phase sensitive detector 23 and configured to convert the second voltage signal into a digital voltage value. The voltage signal outputted from the measurement electrode unit 10 equals to a sum of the first voltage signal and the second voltage signal.

The processor 30 is connected to the analog-to-digital converter 24 and configured to determine, based on the digital voltage value, the resistance $R_x$ between the two measurement electrodes using an equation $$R_x = \frac{R_f * V_o}{V_I},$$

where $V_I$ represents a voltage value of the voltage signal generated by the oscillator, $V_o$ represents the digital voltage value, and $R_f$ represents a resistance of the fixed resistor.

In the embodiment of the present disclosure, through the phase sensitive detector, it is able to remove the influence caused by the capacitance between the two measurement electrodes, thereby ensuring the resistance detection result to be more accurate.

Figure 7:
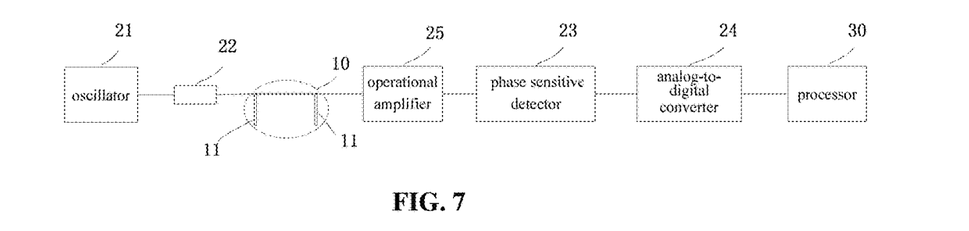
FIG. 7 is another schematic view showing a resistance detection circuit according to an embodiment of the present disclosure.
Figure 8:
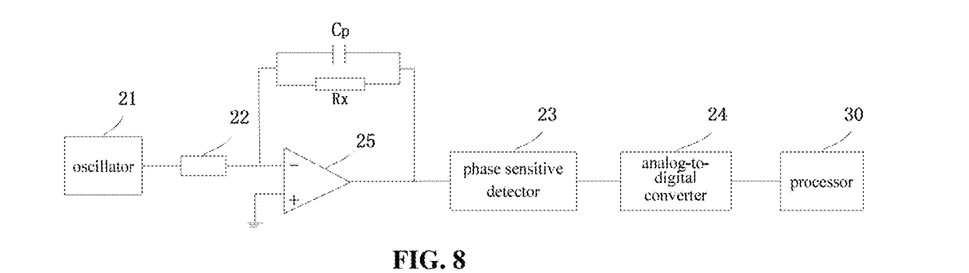
FIG. 8 is an equivalent circuit diagram of the resistance detection circuit in FIG. 7.

Referring to FIG. 7 which is another schematic view showing the resistance detection circuit and FIG. 8 is an equivalent circuit diagram of the resistance detection circuit in FIG. 7 according to an embodiment of the present disclosure, the resistance detection circuit includes: an oscillator 21 configured to generate a voltage signal; a fixed resistor 22, one end of which is connected to the oscillator 21 and the other end of which is connected to the measurement electrode unit 10; an operational amplifier 25 having one input end connected to the measurement electrode unit 10 and the other input end connected to the ground, and configured to amplify a voltage signal from the measurement electrode unit 10; a phase sensitive detector 23 connected to an output end of the operational amplifier 25 and configured to filter the voltage signal amplified by the operational amplifier 25, so as to remove a first voltage signal related to the capacitance between the two measurement electrodes 11, and reserve a second voltage signal related to the resistance between the two measurement electrodes 11; and an analog-to-digital converter 24 connected to the phase sensitive detector 23 and configured to convert the second voltage signal into a digital voltage value.

The processor 30 is connected to the analog-to-digital converter 24 and configured to determine, based on the digital voltage value, the resistance between the two measurement electrodes using an equation $$R_x = \frac{R_f * V_o}{V_I},$$

where $R_x$ represents the resistance between the two measurement electrodes, $V_I$ represents a voltage value of the voltage signal generated by the oscillator, $V_o$ represents the digital voltage value, and $R_f$ represents a resistance of the fixed resistor.

In the embodiment of the present disclosure, through the operational amplifier, it is able to amply the voltage signal to be inputted into the phase sensitive detector, thereby ensuring a filtration result of the phase sensitive detector to be more accurate.

Figure 9:
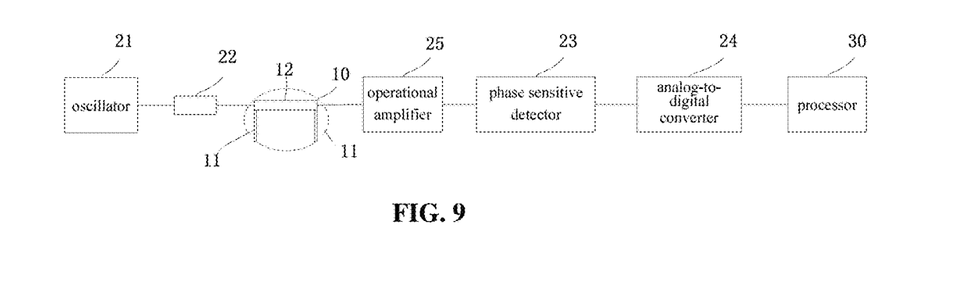
FIG. 9 is yet another schematic view showing a resistance detection circuit according to an embodiment of the present disclosure.

FIG. 9 is yet another schematic view showing the resistance detection circuit according to an embodiment of the present disclosure. The embodiment differs from that in FIG. 7 in that the measurement electrode unit includes two measurement electrodes 11 and a measurement column 12 arranged between, and connected to, the two measurement electrodes 11.

In the embodiment of the present disclosure, through the measurement column 12, it is able to, after the detection of the resistance between the two measurement electrodes, calculate resistivity ρ of the to-be-detected fruit or vegetable, and determine the sugar content of the to-be-detected fruit or vegetable in accordance with the resistivity ρ.

The processor is further configured to determine, based on the resistance between the two measurement electrodes, the resistivity ρ of the to-be-detected fruit or vegetable using an equation $$\rho = \frac{V_o * R_f * S}{V_I * L}$$

and determine the sugar content of the to-be-detected fruit or vegetable in accordance with the resistivity ρ, where $V_I$ represents a voltage value of the voltage signal generated by the oscillator, $V_o$ represents the digital voltage value, $R_f$ represents a resistance of the fixed resistor and it is of a value within the range from 10 to 100Ω, S represents a sectional area of the measurement column, and L represents a length of the measurement column.

Optionally, the fruit and vegetable sugar content detector may further include a storage connected to the processor and configured to store therein a correspondence between the resistivity and the sugar content, and the processor is further configured to inquire the correspondence stored in the storage in accordance with the resistivity of the to-be-detected fruit or vegetable, and determine the sugar content of the to-be-detected fruit or vegetable.

Figure 13:
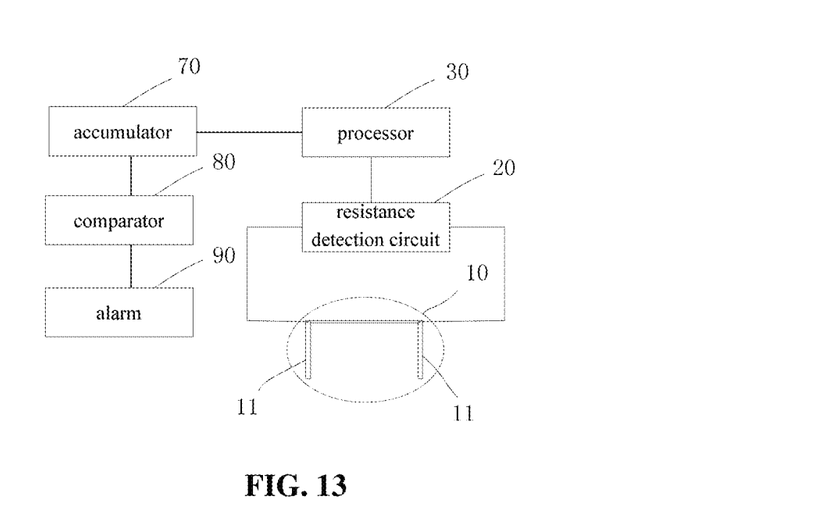
FIG. 13 is still yet another schematic view showing a fruit and vegetable sugar content detector according to an embodiment of the present disclosure.

In order to count the total content of the sugar intake for the user within a predetermined time period (e.g., within one day), optionally, as shown in FIG. 13, the fruit and vegetable sugar content detector may further include: an accumulator 70 connected to the processor 30 and configured to accumulate the sugar contents of the fruit or vegetable detected within the predetermined time period to acquire an accumulated value; a comparator 80 connected to the accumulator 70 and configured to compare the accumulated value with a sugar content threshold, and generate alarm information in the case that the accumulated value exceeds the sugar content threshold; and an alarm 90 connected to the comparator 80 and configured to send an alarm in accordance with the alarm information.

Based on the above structure, the sugar content of the fruit or vegetable may be detected before it is eaten by the user, and the sugar contents of the to-be-detected fruits or vegetables within the predetermined time period may be accumulated. In the case that the accumulated value exceeds the sugar content threshold, it means that the intake sugar content has exceeded a certain standard, and the alarm may be sent to the user.

Figure 10:
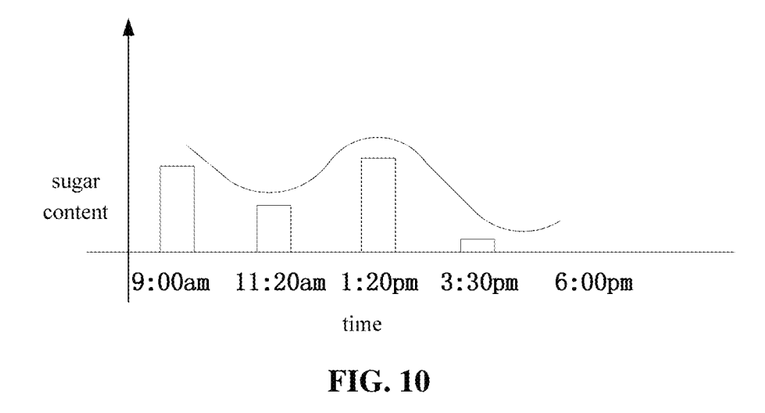
FIG. 10 is a graph showing sugar contents according to an embodiment of the present disclosure.

Optionally, the fruit and vegetable sugar content detector may further include a storage configured to store therein the sugar content information about the fruit or vegetable detected within a predetermined time period and corresponding time points at which those detections are performed. The fruit and vegetable sugar content detector may further include a display configured to display the sugar content information about the fruit or vegetable detected within the predetermined time period and the corresponding time points for those detections in the form of a statistical table as shown in FIG. 10, so that the user may know the sugar intake within the predetermined time period intuitively. Of course, the fruit and vegetable sugar content detector may also transmit, via the communicator, the data stored in the storage to the electronic terminal such as a mobile phone or a personal computer, so as to display or analyze the data on the electronic terminal. In the case that the user is in the hospital, he may provide the data to a doctor, so that the doctor may incorporate the data into a reasonable treatment plan.

In the embodiments of the present disclosure, the fruit and vegetable sugar content detector may be in various forms, e.g., a portable patch that may be conveniently attached onto a bag or any other article of the user. Optionally, the fruit and vegetable sugar content detector may be applied to a wearable electronic device.

In the case that the fruit and vegetable sugar content detector is applied to the wearable electronic device, the wearable electronic device may further include: a housing; a groove arranged on the housing and configured to receive the two measurement electrodes of the measurement electrode unit of the fruit and vegetable sugar content detector, the two measurement electrodes having a first state where the two measurement electrodes are received in the groove and a second state where the two measurement electrodes extend out of the groove; and a control member (not shown in the drawings) arranged on the housing, connected to the measurement electrode unit, and configured to switch the two measurement electrodes between the first state and the second state. Optionally, the control member may be an elastic button.

In the case that the sugar content of the to-be-detected fruit or vegetable needs to be detected by the measurement electrodes, the measurement electrodes may be in the second state, i.e., extend out of the groove, under the control of the controller member. After the detection is completed, the measurement electrodes may be in the first state, i.e., retracted into the groove, under the control of the control member.

In order to provide well appearance, a cover may be arranged on the groove. In the case that the measurement electrodes need to be used, the cover may be opened, and in the case that the measurement electrodes have been retracted into the groove, the cover may be closed.

Figure 11:
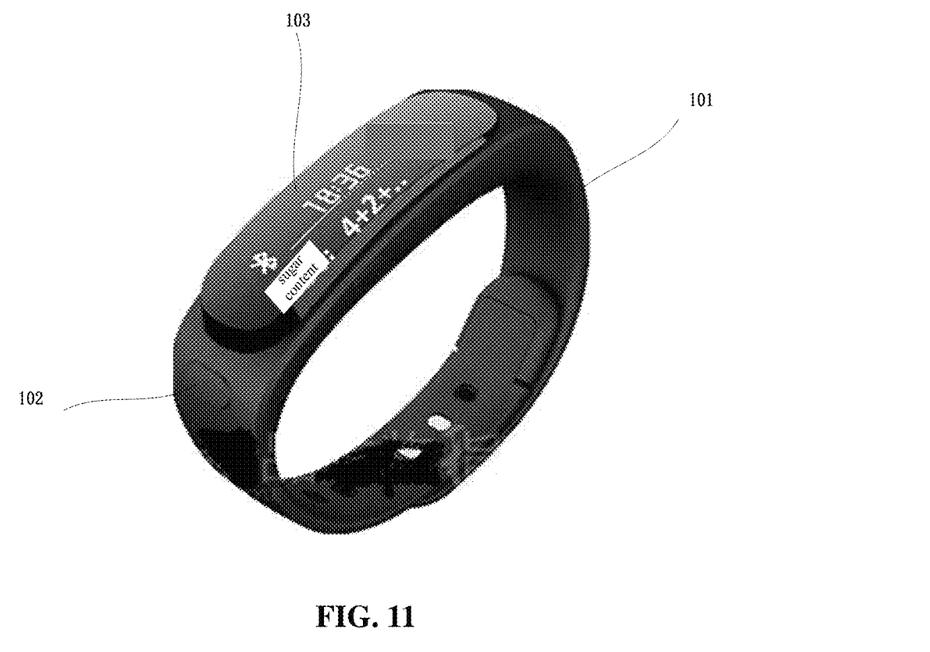
FIG. 11 is a schematic view showing a wearable electronic device according to an embodiment of the present disclosure.

Referring to FIG. 11, apart from the measurement electrode unit, the resistance detection circuit and the processor, the wearable electronic device according to an embodiment of the present disclosure may further include: a housing 101; a groove (not shown) arranged on the housing 101 and a cover 102 arranged on the groove, the two measurement electrodes (not shown) having a first state where the two measurement electrodes are received in the groove and a second state where the two measurement electrodes extend out of the groove; and a control member (not shown) arranged on the housing 101, connected to the measurement electrode unit, and configured to switch the two measurement electrodes between the first state and the second state. The resistance detection circuit and the processor are both arranged inside the housing 101.

In addition, the wearable electronic device may be a smart bracelet, which further includes a display 103 for displaying the sugar content indication information. In addition, the smart bracelet may further have a function of a timepiece for displaying time.

The above are merely the preferred embodiments of the present disclosure. It should be appreciated that, a person skilled in the art may make further modifications and improvements without departing from the principle of the present disclosure, and these modifications and improvements shall also fall within the scope of the present disclosure.

What is claimed is:

1. A fruit and vegetable sugar content detector, comprising:
   a measurement electrode unit comprising two measurement electrodes capable of being inserted into a to-be-detected fruit or vegetable, one end of one of the two measurement electrodes being connected to one end of the other one of the two measurement electrodes;
   a resistance detection circuit connected to the measurement electrode unit and configured to detect a resistance between the two measurement electrodes;
   a processor connected to the resistance detection circuit and configured to determine, in accordance with the detected resistance between the two measurement electrodes, a sugar content of the to-be-detected fruit or vegetable, and generate sugar content indication information, a storage connected to the processor and configured to store therein a correspondence between the resistance and the sugar content, wherein the processor is configured to inquire the correspondence stored in the storage in accordance with the detected resistance between the measurement electrodes, and determine the sugar content of the to-be-detected fruit or vegetable, wherein the measurement electrodes are each of a cylindrical shape, and a cross section of each measurement electrode has a diameter within a range from 5 μm to 15 μm.

2. The fruit and vegetable sugar content detector according to claim 1, wherein the measurement electrodes are each made of a metal.

3. The fruit and vegetable sugar content detector according to claim 1, further comprising an indicator connected to the processor and configured to indicate the sugar content indication information.

4. The fruit and vegetable sugar content detector according to claim 3, wherein the indicator is a display, a sound player, or a combination thereof.

5. The fruit and vegetable sugar content detector according to claim 1, further comprising a communicator connected to the processor and configured to transmit the sugar content indication information to an electronic terminal, so as to enable the electronic terminal to perform indication in response to the sugar content indication information.

6. The fruit and vegetable sugar content detector according to claim 1, wherein the resistance detection circuit comprises:
   an oscillator configured to generate a voltage signal;
   a fixed resistor, one end of which is connected to the oscillator and the other end of which is connected to the measurement electrode unit;
   a phase sensitive detector connected to the measurement electrode unit and configured to filter a voltage signal from the measurement electrode unit, so as to remove a first voltage signal related to a capacitance between the two measurement electrodes and reserve a second voltage signal related to the resistance between the two measurement electrodes; and
   an analog-to-digital converter connected to the phase sensitive detector and configured to convert the second voltage signal into a digital voltage value,
   wherein the processor is connected to the analog-to-digital converter and configured to determine, based on the digital voltage value, the resistance between the two measurement electrodes using an equation $$R_x = \frac{R_f * V_o}{V_I},$$

where $R_x$ represents the resistance between the two measurement electrodes, $V_I$ represents a voltage value of the voltage signal generated by the oscillator, $V_o$ represents the digital voltage value, and $R_f$ represents a resistance of the fixed resistor.

7. The fruit and vegetable sugar content detector according to claim 6, wherein the resistance detection circuit further comprises an operational amplifier arranged between the measurement electrode unit and the phase sensitive detector and configured to amplify the voltage signal from the measurement electrode unit and output the amplified voltage signal to the phase sensitive detector.

8. The fruit and vegetable sugar content detector according to claim 6, wherein the measurement electrode unit further comprises a measurement column arranged between and connected to the two measurement electrodes,
   wherein the processor is further configured to determine, based on the resistance between the two measurement electrodes, a resistivity of the to-be-detected fruit or vegetable using an equation $$\rho = \frac{V_o * R_f * S}{V_I * L}$$

and determine the sugar content of the to-be-detected fruit or vegetable in accordance with the resistivity, where ρ represents the resistivity of the to-be-detected fruit or vegetable, $R_f$ is of a value within the range from 10Ω to 100Ω, S represents a sectional area of the measurement column, and L represents a length of the measurement column.

9. The fruit and vegetable sugar content detector according to claim 1, further comprising:
an accumulator connected to the processor and configured to accumulate sugar contents of the fruit or vegetable detected within a predetermined time period to acquire an accumulated value;
a comparator connected to the accumulator and configured to compare the accumulated value with a sugar content threshold, and generate alarm information in the case that the accumulated value exceeds the sugar content threshold; and
an alarm connected to the comparator and configured to send an alarm in accordance with the alarm information.

10. A wearable electronic device, comprising:
a fruit and vegetable sugar content detector comprising:
a measurement electrode unit comprising two measurement electrodes capable of being inserted into a to-be-detected fruit or vegetable, one end of one of the two measurement electrodes being connected to one end of the other one of the two measurement electrodes;
a resistance detection circuit connected to the measurement electrode unit and configured to detect a resistance between the two measurement electrodes;
a processor connected to the resistance detection circuit and configured to determine, in accordance with the detected resistance between the two measurement electrodes, a sugar content of the to-be-detected fruit or vegetable, and generate sugar content indication information, a storage connected to the processor and configured to store therein a correspondence between the resistance and the sugar content, wherein the processor is configured to inquire the correspondence stored in the storage in accordance with the detected resistance between the measurement electrodes, and determine the sugar content of the to-be-detected fruit or vegetable, wherein the measurement electrodes are each of a cylindrical shape, and a cross section of each measurement electrode has a diameter within a range from 5 μm to 15 μm;
a housing;
a groove arranged on the housing and configured to receive the two measurement electrodes of the measurement electrode unit of the fruit and vegetable sugar content detector, the two measurement electrodes having a first state where the two measurement electrodes are received in the groove and a second state where the two measurement electrodes extend out of the groove; and
a control member arranged on the housing, connected to the measurement electrode unit, and configured to switch the two measurement electrodes between the first state and the second state.

11. The wearable electronic device according to claim 10, wherein the control member is an elastic button.

12. The fruit and vegetable sugar content detector according to claim 7, wherein the measurement electrode unit further comprises a measurement column arranged between and connected to the two measurement electrodes,
wherein the processor is further configured to determine, based on the resistance between the two measurement electrodes, a resistivity of the to-be-detected fruit or vegetable using an equation $$\rho = \frac{V_o * R_f * S}{V_I * L}$$

and determine the sugar content of the to-be-detected fruit or vegetable in accordance with the resistivity, where ρ represents the resistivity of the to-be-detected fruit or vegetable, $R_f$ is of a value within the range from 10Ω to 100Ω, S represents a sectional area of the measurement column, and L represents a length of the measurement column.

* * * * *